(12) United States Patent
Rosenberg et al.

(10) Patent No.: US 8,529,586 B2
(45) Date of Patent: Sep. 10, 2013

(54) NON-INVASIVE SURGICAL LIGATION CLIP SYSTEM AND METHOD OF USING

(75) Inventors: Michael S. Rosenberg, Eagan, MN (US); Timothy J. Claude, Coon Rapids, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 273 days.

(21) Appl. No.: 13/159,939

(22) Filed: Jun. 14, 2011

(65) Prior Publication Data

US 2011/0245848 A1    Oct. 6, 2011

Related U.S. Application Data

(63) Continuation of application No. 12/041,189, filed on Mar. 3, 2008, now Pat. No. 7,967,831, and a continuation of application No. 10/215,216, filed on Aug. 8, 2002, now Pat. No. 7,338,503.

(51) Int. Cl.
*A61B 17/08* (2006.01)
*A61B 17/10* (2006.01)

(52) U.S. Cl.
USPC .......................................... 606/142; 606/157

(58) Field of Classification Search
USPC ................. 606/139, 142, 143, 151, 157, 158, 606/219
See application file for complete search history.

(56) References Cited

U.S. PATENT DOCUMENTS

| | | |
|---|---|---|
| 3,137,027 A | 6/1964 | Birkle |
| 3,279,479 A | 10/1966 | Solomon |
| 3,958,576 A | 5/1976 | Komiya |
| 4,367,746 A | 1/1983 | Derechinsky |
| 4,665,906 A | 5/1987 | Jervis |
| 4,681,107 A | 7/1987 | Kees, Jr. |
| 4,765,335 A | 8/1988 | Schmidt et al. |
| 4,773,132 A | 9/1988 | Eckels |
| 5,062,846 A | 11/1991 | Oh et al. |
| 5,067,957 A | 11/1991 | Jervis |
| 5,190,546 A | 3/1993 | Jervis |
| 5,403,327 A | 4/1995 | Thornton et al. |
| 5,520,701 A | 5/1996 | Lerch |
| 5,597,378 A | 1/1997 | Jervis |
| 5,766,189 A | 6/1998 | Matsuno |
| 5,833,700 A | 11/1998 | Fogelberg et al. |
| 5,897,565 A | 4/1999 | Foster |
| 6,001,110 A | 12/1999 | Adams |
| 6,146,388 A | 11/2000 | McDonald |
| 6,193,732 B1 | 2/2001 | Frantzen et al. |
| 6,193,733 B1 | 2/2001 | Adams |
| 6,228,055 B1 | 5/2001 | Foerster et al. |

(Continued)

FOREIGN PATENT DOCUMENTS

| | | |
|---|---|---|
| JP | 63-267345 | 11/1988 |
| RU | 2213529 | 10/2003 |
| WO | WO 99/62406 | 12/1999 |
| WO | WO 01/37742 | 5/2001 |

OTHER PUBLICATIONS

European Patent Office, European Office Action for Application No. 03784889.2, dated Nov. 25, 2011, 5 pages.

(Continued)

*Primary Examiner* — Julian Woo

(74) *Attorney, Agent, or Firm* — Fish & Richardson P.C.

(57) ABSTRACT

A surgical ligation clip capable of remote deployment through a cannula to engage an anatomical structure.

18 Claims, 10 Drawing Sheets

(56) References Cited

U.S. PATENT DOCUMENTS

| | | |
|---|---|---|
| 6,254,615 B1 | 7/2001 | Bolduc et al. |
| 6,346,112 B2 | 2/2002 | Adams |
| 6,350,269 B1 | 2/2002 | Shipp et al. |
| 6,402,765 B1 | 6/2002 | Monassevitch et al. |
| 6,575,991 B1 | 6/2003 | Chesbrough et al. |
| 6,652,545 B2 | 11/2003 | Shipp et al. |
| 6,679,894 B2 | 1/2004 | Damarati |
| 6,695,854 B1 | 2/2004 | Kayan et al. |
| 6,746,461 B2 | 6/2004 | Fry |
| 6,776,783 B1 | 8/2004 | Frantzen et al. |
| 6,776,784 B2 | 8/2004 | Ginn |
| 2003/0125767 A1 | 7/2003 | Collier et al. |
| 2004/0087987 A1 | 5/2004 | Rosenberg et al. |
| 2004/0111009 A1 | 6/2004 | Adams et al. |

OTHER PUBLICATIONS

Supplemental Search Report EP Application Serial No. 03784889.2, mailed Oct. 2, 2008 11 pages.

European Patent Office, Office Action EP Application No. 03 784 889.2, dated Mar. 26, 2009, 6 pages.

European Patent Office, Official Action for Application No. 03784889.2-2310, dated Mar. 11, 2010, 28 pages.

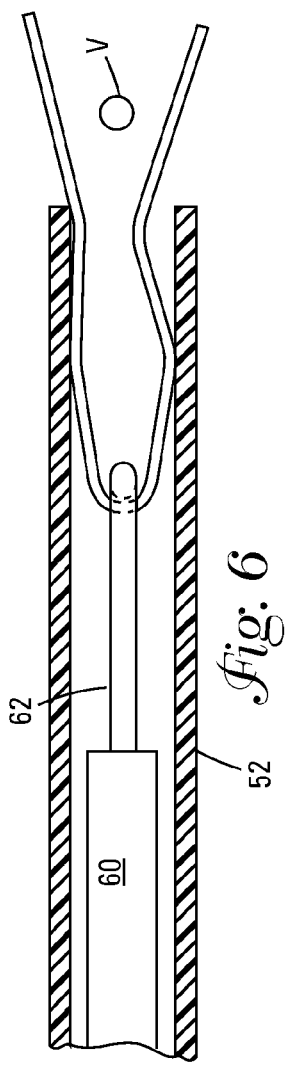
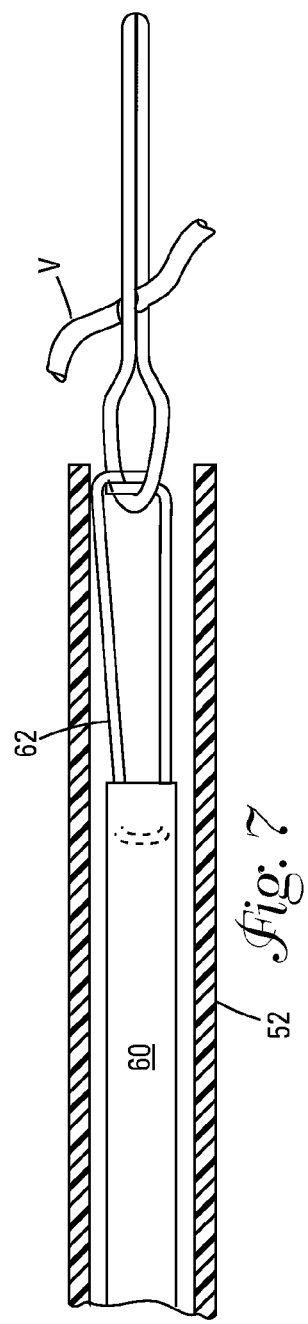
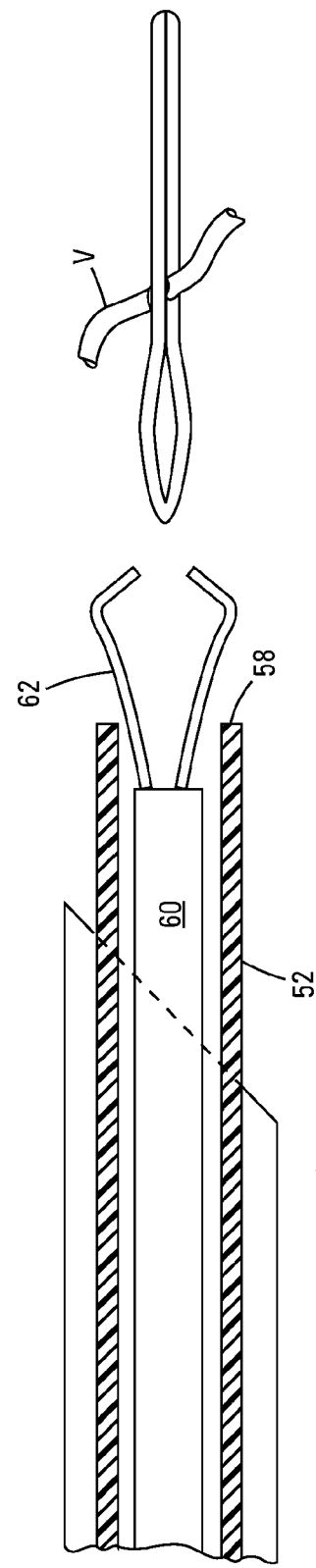
Fig. 6
Fig. 7
Fig. 8

NON-INVASIVE SURGICAL LIGATION CLIP SYSTEM AND METHOD OF USING

CROSS-REFERENCE TO RELATED APPLICATION(S)

This application is a continuation application of U.S. application Ser. No. 12/041,189, filed on Mar. 3, 2008 now U.S. Pat. No. 7,967,831, by Michael S. Rosenberg et al. and entitled "NON-INVASIVE SURGICAL LIGATION CLIP SYSTEM AND METHOD OF USING," which is a continuation application of U.S. application Ser. No. 10/215,216, filed on Aug. 8, 2002 now U.S. Pat. No. 7,338,503,by Michael S. Rosenberg et al. and entitled "NON-INVASIVE SURGICAL LIGATION CLIP SYSTEM AND METHOD OF USING." The disclosures of these earlier applications are fully incorporated herein by reference.

FIELD OF THE INVENTION

The invention relates to ligation clips used in non-invasive surgical procedures.

BACKGROUND

Non-invasive surgical procedures are increasingly popular among physicians, patients and insurance companies due to the decreased trauma and consequent healing time to the patient and decreased overall cost resulting from shortened hospital stays. Such surgical procedures allow physicians to access remote regions of a patient's body to perform surgery without having to make major incisions in the patient's body. One form of non-invasive procedure requires the physician to create small incisions proximate the area underlying which the procedure is to be performed. Often, several such minor incisions are created, through which the physician inserts fiber optic viewing systems and micro instruments able to perform the procedure. In another type of procedure, the interior of the body is accessed by means of navigating viewing systems and instruments through the vasculature of the patient to the internal treatment site, following which, the procedure is performed. In both types of procedures, it is often necessary for the physician to be able to ligate blood vessels that may be intentionally or inadvertently severed. Additionally, clamping off of aneurysms and fistulas may also be required.

Existing systems for ligating during non-invasive surgery include a device for remotely applying surgical conventional stainless steel staples, as disclosed in U.S. Pat. No. 5,403,327, to Thronton et al. Such a system is, however, limited, to a rigid-shafted, straight-line instrument, and thus is inapplicable to many procedures where a more tortuous introductory path is required to access the treatment site. A further disadvantage of stainless steel clips deals with the relatively low elasticity of stainless steel, which, when sufficiently bent, tends to remain in its bent position. Thus, repositioning the clip after initial placement using the system in Thronton et al. is impossible without further open surgery. U.S. Pat. No. 6,001,110, to Adams, proposes a hemostatic clip constructed of nitinol that is superelastic at human body temperatures. The Adams clip, in one embodiment, is trained to be in a "U" configuration when in an undeformed state. Prior to application of the Adams clip, its prongs are forced open against its trained inward tendency, the clip is navigated proximate the structure to be clamped, and then the prongs are released around the structure. The structure is clamped off, resulting from the prongs attempting to return to their original inward position, restrained only by the tissue being clamped. The Adams device is limited to a rigid, straight-line hypotube delivery system, restricting the uses to which it may be directed. What is clearly needed, therefore, is a surgical ligating clip that can be navigated via the patient's vascular system to remote sites in the patient's body and installed. Additionally desirable would be the ability to reposition the clip following initial placement.

SUMMARY OF THE INVENTION

In one embodiment, the invention comprises a clip defining an unstressed shape. A first opposing jaw defines a clamping portion and a second opposing jaw defines a clamping portion. At least the first jaw defines a flexing portion having a different shape than the clamping portion of the first jaw, and the flexing portion is capable of being stressed so as to alter its shape and then resuming the unstressed shape when no longer being stressed. The first and second jaws are unattached at a first point of the clamping portions of the first and second jaws, which allows the first and second jaws to be able to separate apart from each other. When the flexing portion of the first jaw is stressed so as to alter its shape, the clamping portion of the first jaw moves in relation to the clamping portion of the second jaw. This causes the clamping portion of the first jaw to separate from the clamping portion of the second jaw.

In another embodiment, the invention comprises a clip defining an unstressed shape. The clip includes first and second opposing, longitudinally configured jaws, with the first and second jaws each defining a clamping portion and a flexing portion. The flexing portions are capable of being stressed so as to alter the unstressed shape of the flexing portions and then resuming he unstressed shape when the clip is no longer being stressed. The first and second jaws are unattached at a first point of the clamping portions which allows the first and second jaws to be able to separate apart from each other. Stressing the flexing portions of the first and second jaw toward each other therefore causes the clamping portions of the first jaw and second jaw to move away from each other.

In yet another embodiment, the invention comprises a clip system. The system comprises a clip having a lateral dimension and a longitudinal dimension. The clip further defines an unstressed shape. A first opposing jaw defines a clamping portion and a second opposing jaw defines a clamping portion. At least the first jaw defines a flexing portion having a different shape than the clamping portion of the first jaw, and the flexing portion is capable of being stressed so as to alter its shape and then resuming the unstressed shape when no longer being stressed. The first and second jaws are unattached at a first point of the clamping portions of the first and second jaws, which allows the first and second jaws to be able to separate apart from each other. When the flexing portion of the first jaw is stressed so as to alter its shape, the clamping portion of the first jaw moves in relation to the clamping portion of the second jaw. This causes the clamping portion of the first jaw to separate from the clamping portion of the second jaw. The system also comprises a cannula. The cannula includes a tubular member defining walls and a lumen, and a proximal end and a distal end. The lumen has a sufficient inner dimension to accommodate the clip when the flexing portion of the first jaw is stressed toward the second jaw, thus reducing the lateral dimension of the clip and increasing the longitudinal dimension of the clip. This allows the flexing portion of the first jaw to be stressed to reduce the lateral dimension to be smaller than the inner dimension of the lumen of the cannula. Following stressing of the clip it is loaded into the lumen so that the clamping portion faces the distal end of the cannula, which constrains the flexing portion and the clamping portion within the cannula. Advancing the clamping portions of the first and second jaws of the clip from the distal end of the cannula results in the clamping portions of the first and second jaws spreading apart from each other as long as the flexing portion of the first jaw remains constrained within the lumen of the cannula. Further advancing the clip from the distal end of the cannula so that the flexing portion of the first jaw is released from the cannula results in the clamping portions of the first and second jaws attempting to resume the unstressed, parallel configuration.

A further embodiment of the invention comprises a clip system. The system comprises a clip defining an unstressed shape. The clip includes first and second opposing, longitudinally configured jaws, with the first and second jaws each defining a clamping portion and a flexing portion. The flexing portions are capable of being stressed so as to alter the unstressed shape of the flexing portions and then resuming he unstressed shape when the clip is no longer being stressed. The first and second jaws are unattached at a first point of the clamping portions which allows the first and second jaws to be able to separate apart from each other. Stressing the flexing portions of the first and second jaw toward each other therefore causes the clamping portions of the first jaw and second jaw to move away from each other. The system also comprises a cannula. The cannula includes a tubular member defining walls and a lumen, and proximal and a distal ends. The lumen has a sufficient inner dimension to accommodate the clip when the flexing portion of the first jaw is stressed toward the second jaw, thus reducing the lateral dimension of the clip and increasing the longitudinal dimension of the clip. The flexing portions of the first and second jaw are stressed to reduce the lateral dimension to be smaller than the inner dimension of the lumen of the cannula and the clip is loaded into the lumen so that the clamping portion faces the distal end of the cannula, which constrains the flexing portion and the clamping portion within the cannula. Advancing the clamping portions of the first and second jaws of the clip from the distal end of the cannula results in the clamping portions of the first and second jaws spreading apart from each other as long as the flexing portions of the first and second jaws remain constrained within the lumen of the cannula. Further advancing the clip from the distal end of the cannula so that the flexing portions of the first and second jaws are released from the cannula results in the clamping portions of the first and second jaws attempting to resume the unstressed, parallel configuration.

In yet a further embodiment, the invention comprises a method of using a clip system. The method includes the step of providing a clip system comprising a clip having a lateral dimension and a longitudinal dimension. The clip defines an unstressed shape. A first opposing jaw defines a clamping portion and a second opposing jaw defines a clamping portion. At least the first jaw defines a flexing portion having a different shape than the clamping portion of the first jaw, so the flexing portion is capable of being stressed so as to alter its shape and then resume the unstressed shape when no longer being stressed. The first and second jaws are unattached at a first point of the clamping portions of the first and second jaws, which allows the first and second jaws to be able to separate apart from each other. When the flexing portion of the first jaw is stressed so as to alter its shape, the clamping portion of the first jaw moves in relation to the clamping portion of the second jaw, separating the clamping portion of the first jaw from the clamping portion of the second jaw. Determining a structure requiring clamping is necessary as is navigating the clip system to a remote internal area of a patient's body. When the clip system is navigated to the remote area of a patient's body, the clip is advanced distally from the cannula toward the structure requiring clamping so that the clamping portions of the clip are spread apart from each other. The clip is further distally advanced to move the spread apart clamping portions of the clip around the structure to be clamped. Finally, the clip is further distally advanced from the cannula so that the flexing portions of the jaws are advanced distally from the cannula to allow the flexing portions to resume their non-stressed shape, resulting in the clamping portions of the jaws returning toward their non-stressed parallel configuration, resulting in clamping of the desired structure. Following initial placement, if repositioning of the clip is necessary or desired, the clip is withdrawn in a proximal direction into the cannula a sufficient distance to stress the flexing portions of the first and second jaws. This results in spreading apart the clamping portions of the first and second jaws and the unclamping of the initially clamped structure. The clip is then repositioned and the first and second jaws are again advanced in a distal direction from the cannula allowing the clamping portions of the first and second jaws to clamp the structure.

BRIEF DESCRIPTION OF THE DRAWINGS

FIG. 4a shows a cross section taken along line A-A of the clamping portion of the clip shown in FIG. 4, including the "D" shaped wire from which it is made.

FIG. 6 shows the clip advanced from the cannula so the jaws are opened.

FIG. 7 shows a the clip further advanced from the cannula so that the jaws after surrounding the vessel attempt to close resulting in occlusion of the clamped vessel.

FIG. 8 shows a side view of the ligation clip completely emerged from the cannula.

DETAILED DESCRIPTION OF THE INVENTION INCLUDING A BEST MODE

Nomenclature

10 Ligation Clip (First Embodiment)
12 First Jaw
14 Second Jaw

| | |
|---|---|
| 16 Clamping Portion (First Jaw) | 524a Distal End (First Jaw) |
| 18 Clamping Portion (Second Jaw) | 524b Distal End (Second Jaw) |
| 20 Flexing Portion (First Jaw) | 526 Proximal End |
| 22 Flexing Portion (Second Jaw) | 600 Ligation Clip (Seventh Embodiment) |
| 24a Distal End (First Jaw) | 612 First Jaw |
| 24b Distal End (Second Jaw) | 614 Second Jaw |
| 26 Proximal End | 616 Clamping Portion (First Jaw) |
| 50 Clip System | 617 Indentation (First Jaw) |
| 52 Cannula | 618 Clamping Portion (Second Jaw) |
| 54 Cannula Wall | 620 Flexing Portion (First Jaw) |
| 56 Lumen | 624a Distal End (First Jaw) |
| 58 Distal End of Cannula | 624b Distal End (Second Jaw) |
| 60 Push Rod | 626 Proximal End |
| 62 Clip Lock | 800 Ligation Clip (Eighth Embodiment) |
| 100 Ligation Clip (Second Embodiment) | 812 First Jaw |
| 112 First Jaw | 814 Second Jaw |
| 114 Second Jaw | 816 Clamping Portion (First Jaw) |
| 116 Clamping Portion (First Jaw) | 818 Clamping Portion (Second Jaw) |
| 118 Clamping Portion (Second Jaw) | 820 Flexing Portion (First Jaw) |
| 120 Flexing Portion (First Jaw) | 822 Flexing Portion (Second Jaw) |
| 122 Flexing Portion (Second Jaw) | 824a Distal End (First Jaw) |
| 126 Proximal End | 824b Distal End (Second Jaw) |
| 200 Ligation Clip (Third Embodiment) | 826 Proximal End |
| 212 First Jaw | 910 Ribbon Wire |
| 214 Second Jaw | 912 Round Wire |
| 216 Clamping Portion (First Jaw) | 914 D-Shaped Wire |
| 218 Clamping Portion (Second Jaw) | V Vessel |
| 220 Flexing Portion (First Jaw) | |
| 222 Flexing Portion (Second Jaw) | |
| 224a Distal End (First Jaw) | |
| 224b Distal End (Second Jaw) | |
| 226 Proximal End | |
| 300 Ligation Clip (Fourth Embodiment) | |
| 312 First Jaw | |
| 314 Second Jaw | |
| 316 Clamping Portion (First Jaw) | |
| 318 Clamping Portion (Second Jaw) | |
| 320 Flexing Portion (First Jaw) | |
| 322 Flexing Portion (Second Jaw) | |
| 324a Distal End (First Jaw) | |
| 324b Distal End (Second Jaw) | |
| 326 Proximal End | |
| 328 Weld | |
| 330 Fitting | |
| 332 Pusher | |
| 352 Cannula | |
| 354 Cannula Wall | |
| 356 Lumen | |
| 358 Distal End of Cannula | |
| 400 Ligation Clip (Fifth Embodiment) | |
| 412 First Jaw | |
| 414 Second Jaw | |
| 416 Clamping Portion (First Jaw) | |
| 417a Grips (First Jaw) | |
| 417b Grips (Second Jaw) | |
| 418 Clamping Portion (Second Jaw) | |
| 420 Flexing Portion (First Jaw) | |
| 422 Flexing Portion (Second Jaw) | |
| 424a Distal End (First Jaw) | |
| 424b Distal End (Second Jaw) | |
| 426 Proximal End | |
| 500 Ligation Clip (Sixth Embodiment) | |
| 512 First Jaw | |
| 514 Second Jaw | |
| 516 Clamping Portion (First Jaw) | |
| 518 Clamping Portion (Second Jaw) | |
| 520 Flexing Portion (First Jaw) | |

Construction

Figure 1:
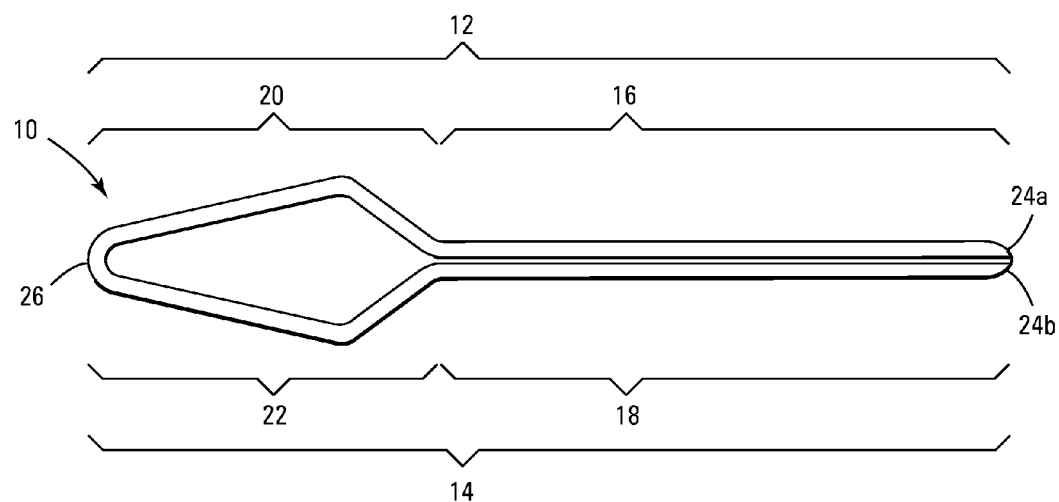
FIG. 1 shows a side view of the ligation clip.
Figure 2:
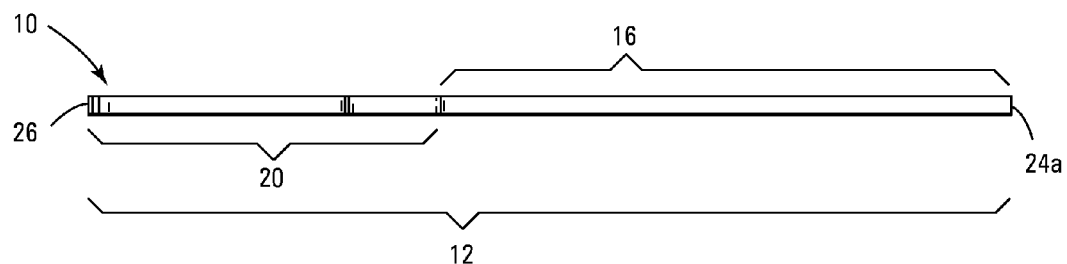
FIG. 2 shows a top view of the ligation clip shown in FIG. 1.

FIG. 1 shows a first embodiment of the ligation clip 10. The ligation clip 10 comprises at least a first 12 and second jaw 14, which have a longitudinal orientation. The first jaw 12 defines a clamping portion 16 and a flexing portion 20, and the second jaw 14 similarly defines a clamping portion 18 and a flexing portion 22. In this embodiment, the clamping portions 16, 18 are parallel with each other and should contact or nearly contact each other when in a non-stressed state. Both first 12 and second 14 jaws define a distal end 24a, 24b, which are not connected together and therefore able to be separated from each other. A proximal end 26 is likewise defined longitudinally opposite the distal end 24a, 24b, however, at the proximal end 26 the first 12 and second 14 jaws are attached. The attachment may take the form of the entire clip 10, 100, 200, 300, 400, 500, 600, 800 being formed from a single length of wire as shown in FIGS. 1-11 and FIGS. 13-14. Alternatively, the attachment may be two separate pieces of wire 312, 314 held together by a welded joint 328 and a threaded sleeve 330 as shown in FIG. 12. As shown in FIGS. 1-2, and 5-14, the flexing portions 20, 22, 120, 122, 320, 322, 420, 422, 520, 620, 820, 822 are formed so as to have bends with substantially straight portions extending away from the longitudinal axis of the first and second 12, 14, 112, 114, 212, 214, 312, 314, 412, 414, 512, 514, 612, 614, 812, 814 jaws. The invention contemplates other angles for the flexing portions 20, 22, 120, 122, 320, 322, 420, 422, 520, 620, 820, 822, thus, other angles can also be formed so as to create different angular relationships to the longitudinal axis of the first 112 and second 114 jaws. An angular difference also necessitates a difference in the ratio of the length of the flexing portions 20, 22, 120, 122, 320, 322, 420, 422, 520, 620, 820, 822 to the clamping portions 16, 18, 116, 118, 216, 218, 316, 318, 416, 418, 516, 518, 616, 618, 816 and 818.

Figure 3:
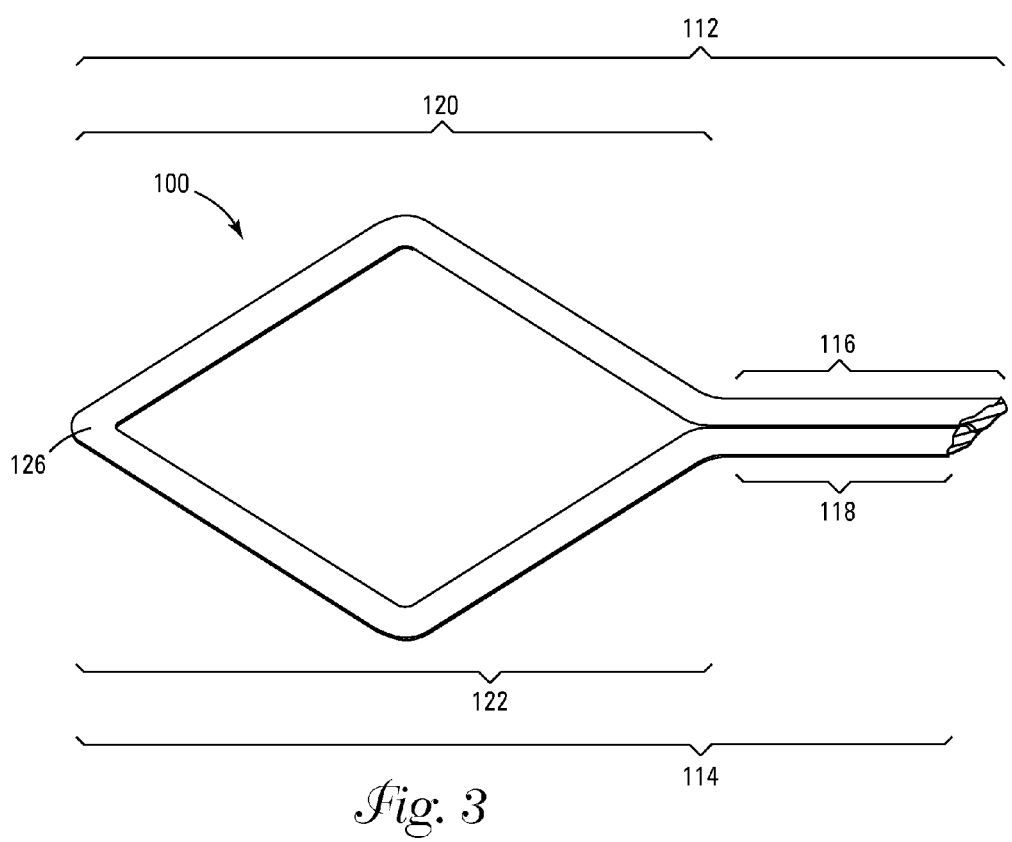
FIG. 3 shows a side view of an alternative embodiment of the ligation clip.

In a second embodiment, as shown in FIG. 3, the ligation clip 100 comprises at least a first 112 and second jaw 114, which have a longitudinal orientation. The first jaw 112 defines a clamping portion 116 and a flexing portion 120. The second jaw 114 similarly defines a clamping portion 118 and a flexing portion 122. In this embodiment, the clamping portions 116, 118 are parallel with each other and should contact each other when in a non-stressed state. As discussed above, the flexing portions 120, 122 define a different angle than shown in the embodiment of FIG. 1. Both first 112 and second 114 jaws define distal ends, 124a, 124b, which are not connected together and therefore able to separate. A proximal end 126 is likewise defined longitudinally opposite the distal ends 124a, 124b, however, at the proximal end 126 the first 112 and second 114 jaws are attached.

Figure 4:
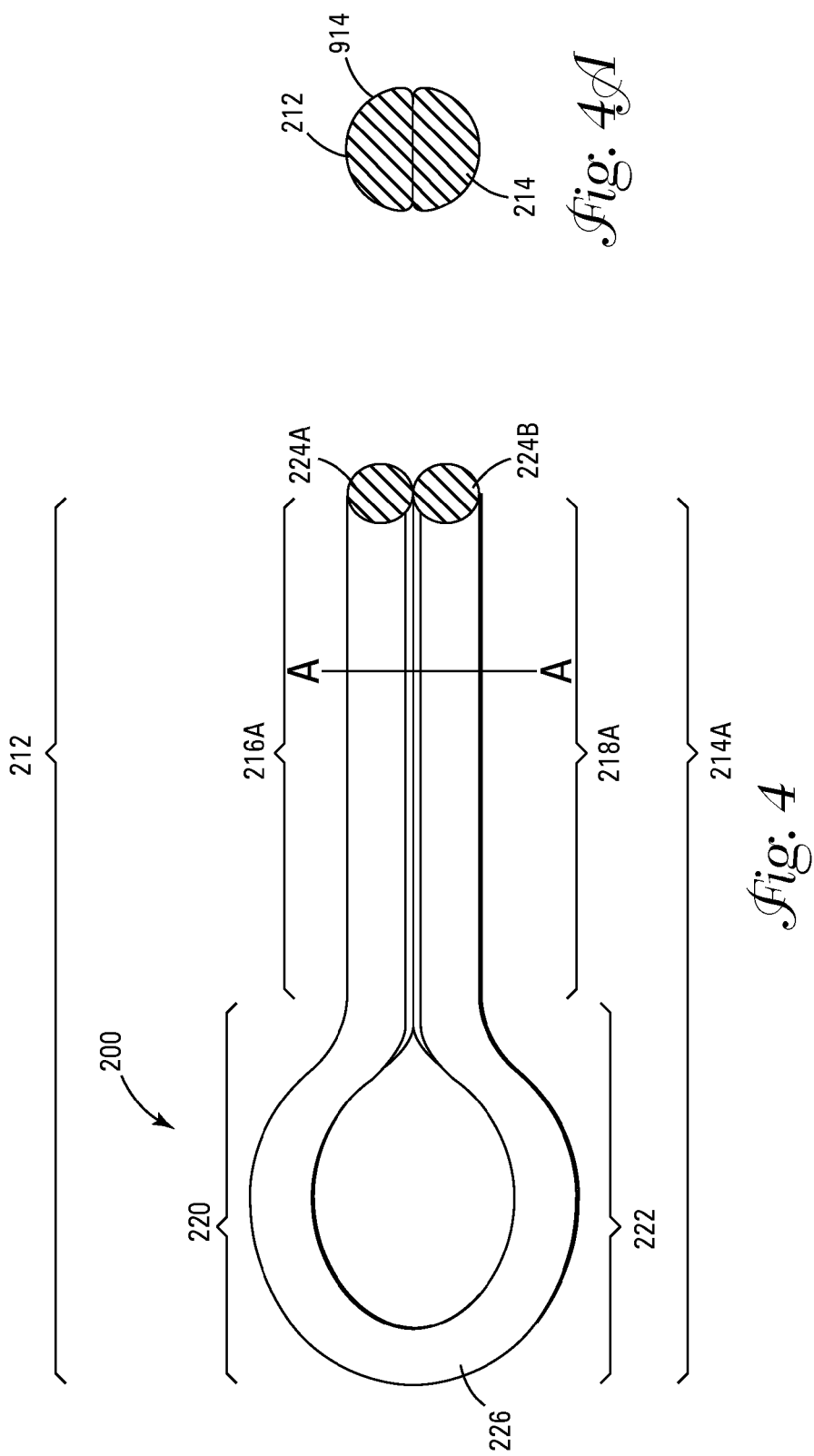
FIG. 4 shows a perspective view of a further alternative embodiment of the ligation clip.
Figure 15:
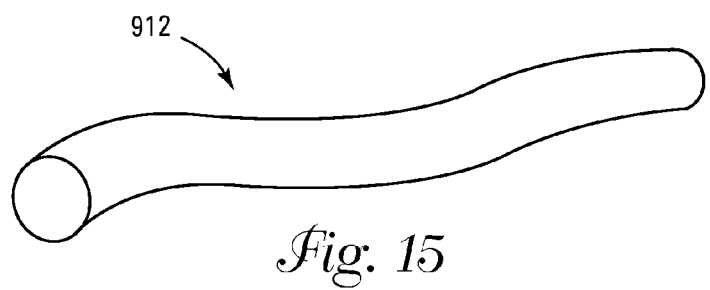
FIG. 15 shows a perspective view of a length of round wire.

A third embodiment of the ligation clip 200 is shown in FIG. 4, wherein the flexing portions 220, 222 are formed in a curved manner. In all other aspects, the third embodiment of the ligation clip 200 is structurally and functionally similar to the embodiments shown in FIGS. 1-3 and 5-8. A first jaw 212 defines a clamping portion 216 which terminates at a distal end (not shown) and a flexing portion 220. A second jaw 214 defines a clamping portion 218 which terminates at a distal end (not shown) and a flexing portion 222. The clamping portion 216 of the first jaw 212 when unstressed is parallel with and contacts or nearly contacts the clamping portion 218 of the second jaw 214. The first 212 and second 214 jaws are joined together at a proximal end 226. FIG. 4a shows a cross-section taken along line A-A of the clamping portions 216, 218 of the third embodiment 200 to illustrate "D" shaped wire. Other wire shapes including ribbon wire as shown in FIG. 15, round wire as shown in FIG. 16 and third round (120 degree) wire (not shown) are also contemplated by and therefore within the scope of the invention.

Figure 9:
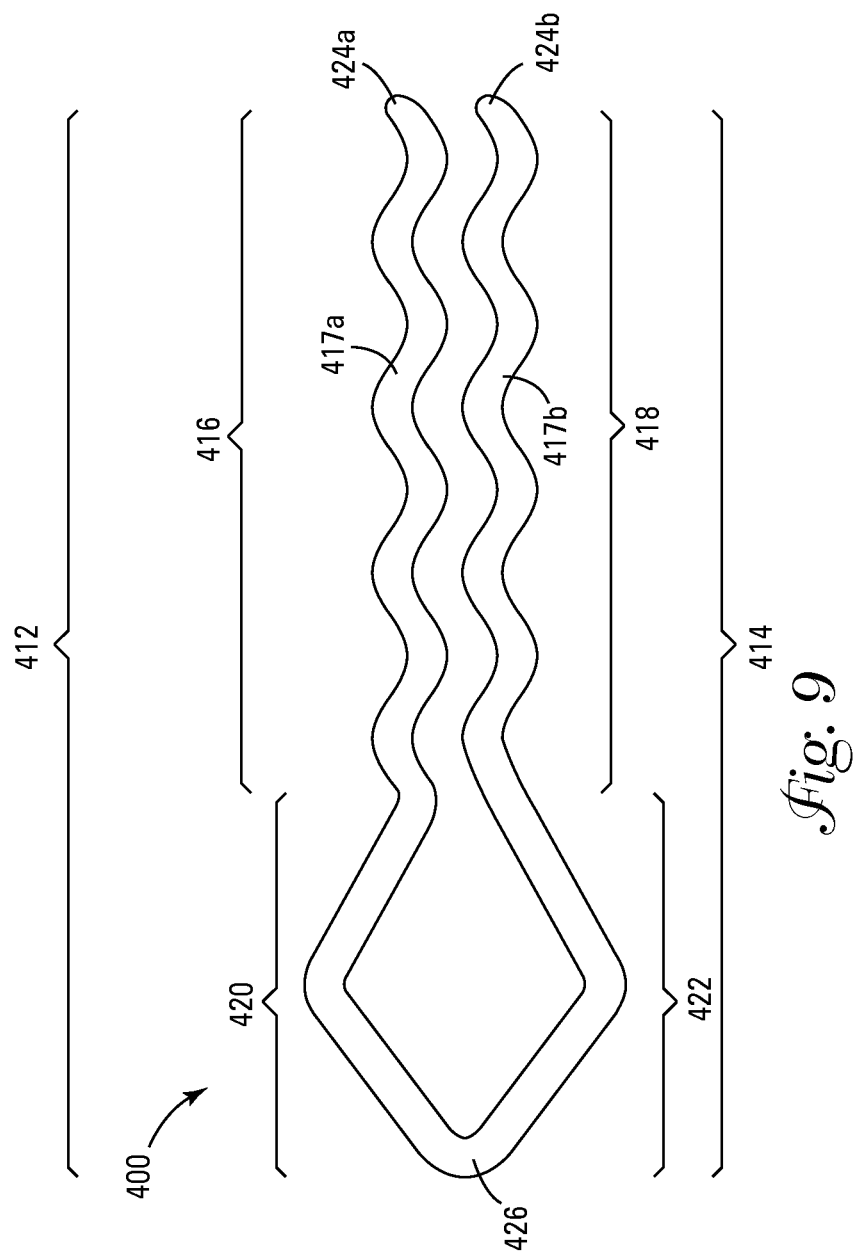
FIG. 9 shows a side view of the ligation clip having wavy, interlocking inner edges on the clamping portions of the jaws.

Several additional embodiments of the ligation clip are also disclosed in the specification. FIG. 9 illustrates a fourth embodiment of the clip 400 which is similar to the embodiment 10 shown in FIG. 1 except that the clamping portions 416, 418 are provided with a series of wave-like grips 417a, 417b to facilitate clamping. The grips 417a, 417b may be formed into the wire so as to be matching to further increase the clamping ability of the clip 400, however including this feature will increase the complexity and cost of manufacturing due to greater manufacturing precision involved. The ligation clip 400 defines at least a first 412 and second jaw 414, which have a longitudinal orientation. The first jaw 412 defines a clamping portion 416 and a flexing portion 420. The second jaw 414 similarly defines a clamping portion 418 and a flexing portion 422. In this embodiment, the clamping portions 416, 418 should contact each other or nearly so when in a non-stressed state. Both first 412 and second 414 jaws define distal ends, 424a, 424b, which are not connected together and therefore able to separate. A proximal end 426 is likewise defined longitudinally opposite the distal end 424a, 424b, however, at the proximal end 426 the first 412 and second 414 jaws are attached.

Figure 10:
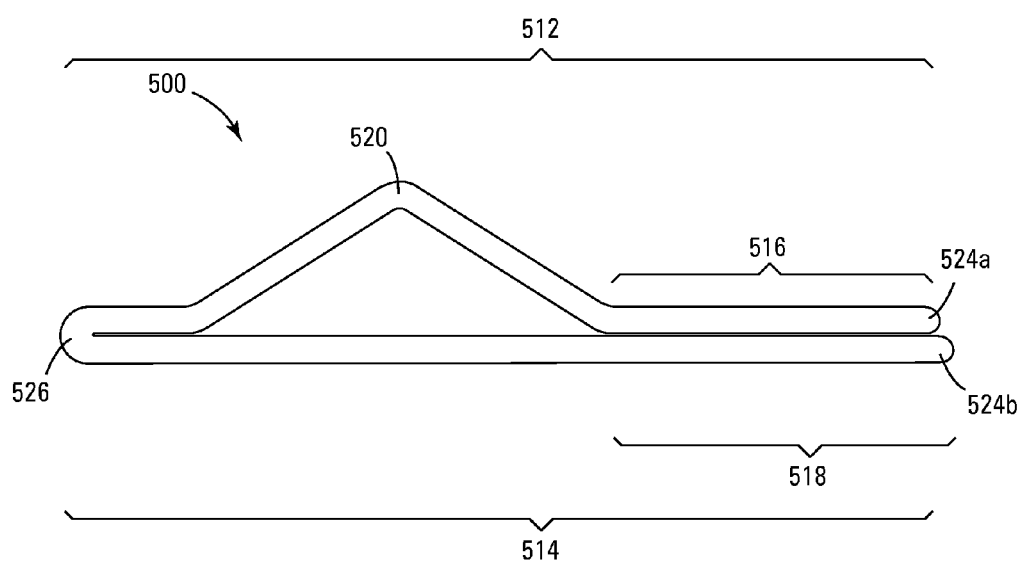
FIG. 10 shows a side view of an embodiment of the ligation clip having one jaw with a flexing portion.

FIG. 10 shows a fifth embodiment of the clip 500 which is similar to the clip 10 of FIG. 1 except for the lack of a flexing portion on the second jaw 514. This necessitates a longer clamping section 518 on the second jaw 514. The effect of only a single flexing portion 520 is to lessen the amount of force exerted by the clip 500 as a result of clamping. The ligation clip 500 defines at least a first 512 and second jaw 514, which have a longitudinal orientation. The first jaw 512 defines a clamping portion 516 and a flexing portion 520. The second jaw 514, however, defines a only a clamping portion 518. In this embodiment, the clamping portions 516, 518 are parallel with each other and should contact each other or nearly so when in a non-stressed state, only along that portion of their lengths where the clamping portion 516 of the first jaw 512 corresponds with the clamping portion 518 of the second jaw 514. Both first 512 and second 514 jaws define distal ends, 524a, 524b, which are not connected together and therefore separate. A proximal end 526 is likewise defined longitudinally opposite the distal end 524a, 524b, however, at the proximal end 526 the first 512 and second 514 jaws are attached.

Figure 11:
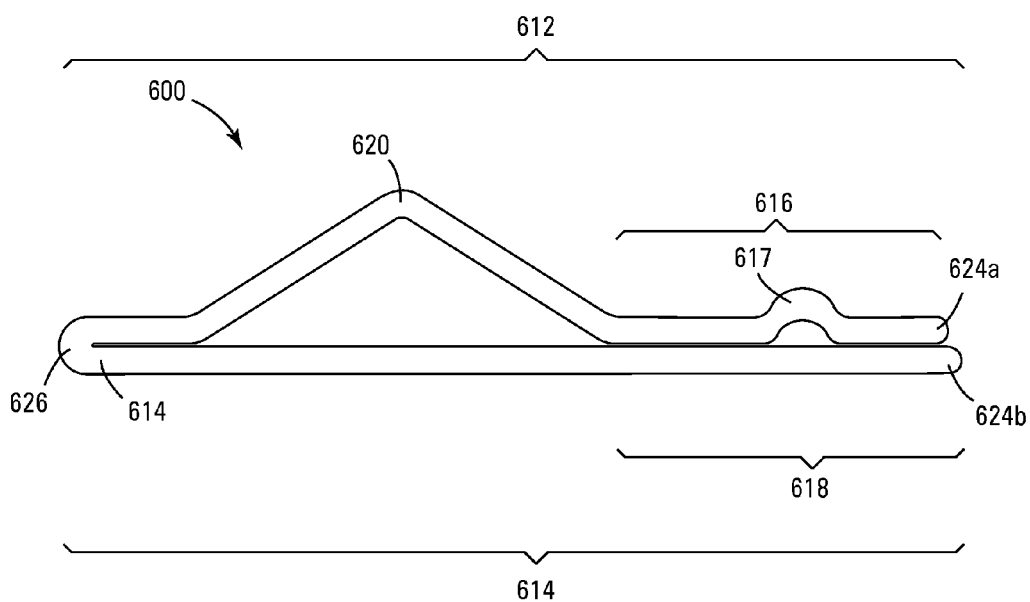
FIG. 11 shows a side view of an alternative embodiment of the ligation clip.
Figure 12:
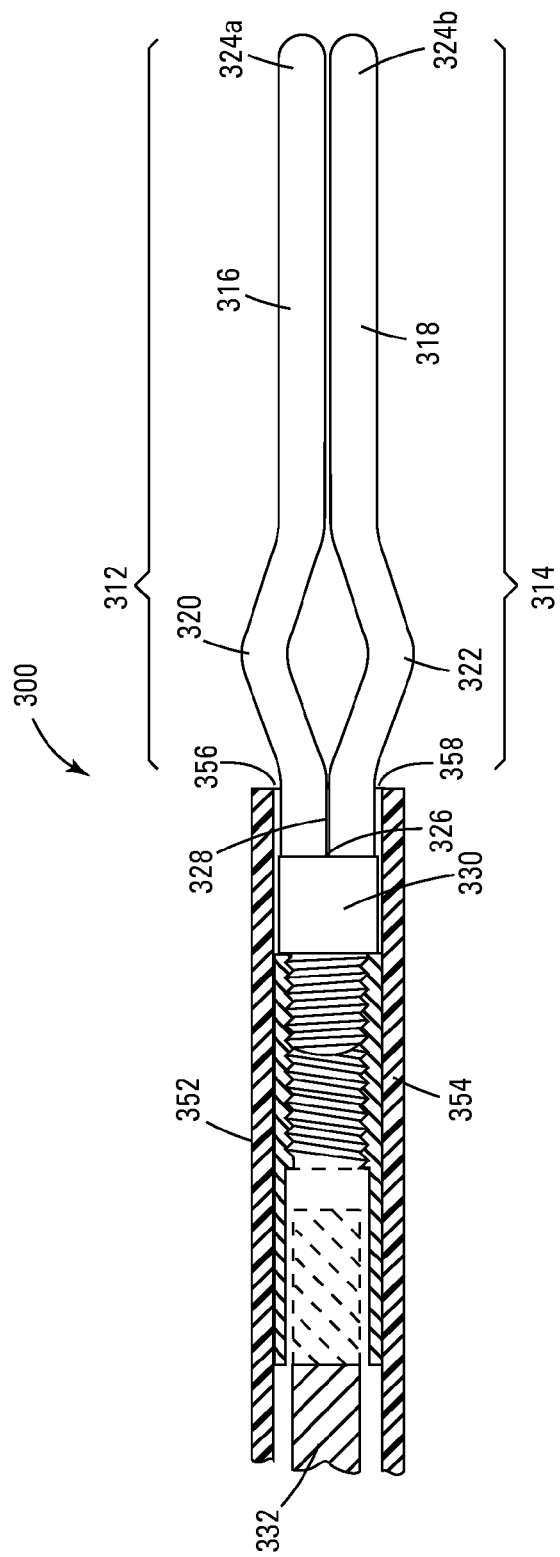
FIG. 12 shows a side view of another embodiment of the ligation clip.

FIG. 11 shows a sixth embodiment of the clip 600, which is similar to the clip 500 shown in FIG. 10. The difference is that the clip 600 has an indentation 617 in the clamping portion 616 of the first jaw 612. The indentation 617 allows the clip 600 to exert less force against the clamped anatomical structure should less force be necessary. An additional advantage to having an indentation 617 is that it may help to guide or seat the structure and prevent the structure to be clamped (not shown) from being forced out of the clip 600 during the clamping procedure. The ligation clip 600 defines at least a first 612 and second jaw 614, which have a longitudinal orientation. The first jaw 612 defines a clamping portion 616 and a flexing portion 620. The second jaw 614, however, defines only a clamping portion 618. In this embodiment, the clamping portions 616, 618 should contact at least a portion of each other or nearly so when in a non-stressed state. Both first 612 and second 614 jaws define a distal end 624a, 624b, which are not connected together and therefore able to separate. A proximal end 626 is likewise defined longitudinally opposite the distal ends 624a, 624b, however, at the proximal end 626 the first 612 and second 614 jaws are attached.

Figure 13:
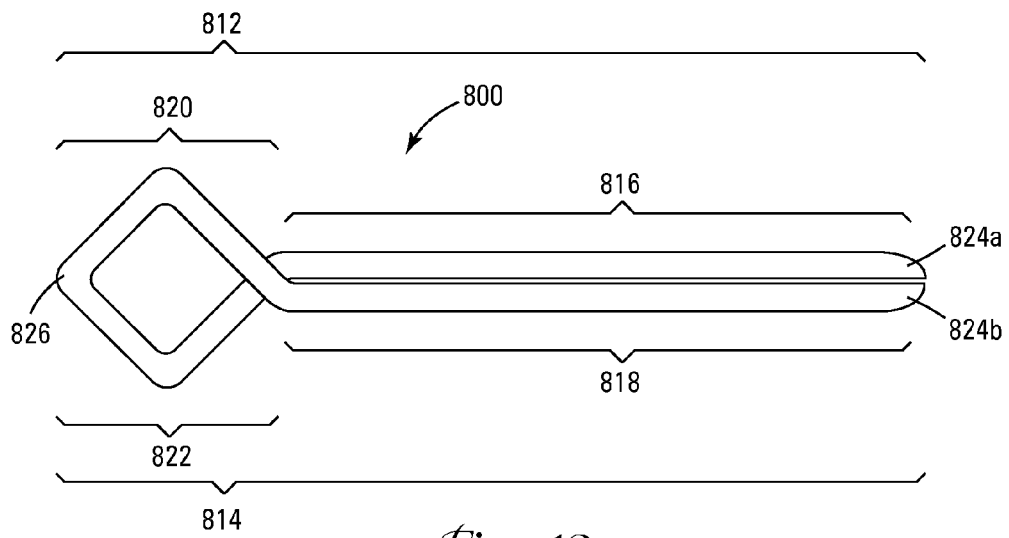
FIG. 13 shows a side view of an embodiment of the ligation clip having jaws with crossed clamping portions.
Figure 14:
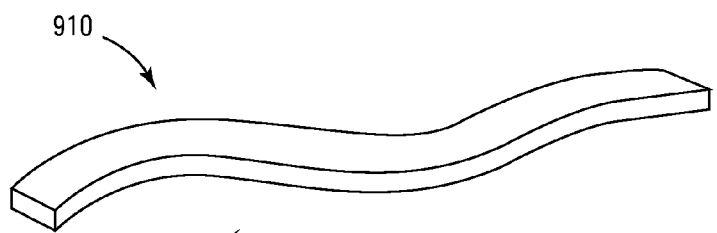
FIG. 14 shows a perspective view of a length of ribbon wire.

FIG. 13 shows a seventh embodiment of the clip 800 that defines a first jaw 812 and a second jaw 814. The first jaw 812 defines a clamping portion 816 which terminates at a distal end 824a and a flexing portion 820. In a similar manner, the second jaw 814 defines a clamping portion 818, which terminates at a distal end 824b and a flexing portion 822. The first jaw 812 and second jaw 814 are joined at a proximal end 826 of the clip 800. The clamping portions 816, 818 cross over each other so as to exert a greater amount of force against a clamped anatomical structure (not shown in FIG. 13).

In a preferred embodiment, the clip 10, 100, 200, 300, 400, 500, 600, 800 is formed from a single length of nitinol wire that has been processed to exhibit superelasticity at human body temperature (around 37 degrees C.). The invention also contemplates forming the clip 10, 100, 200, 300, 400, 500, 600, 800 from nitinol processed to exhibit thermal shape memory characteristics at human body temperature. Nitinol is an approximate stoichiometric alloy of nickel and titanium, however, other elements such as vanadium, are sometimes added in small amounts to alter the mechanical characteristics of the alloy. Its chemical composition and its processing history primarily determine the particular mechanical properties of a shape memory/superelastic metallic alloy. In general, such an alloy will exist in either one or the other, or combinations of two crystallographic phases. Austenite is the parent crystallographic phase and exists at higher temperatures. Martensite is the other phase and it is formed by either subjecting the alloy to lower temperatures or by placing mechanical or physical stress on the alloy while it is in the austenitic phase. Transition temperatures between these two phases can be experimentally determined for a particular alloy. Alloy chemistry and thermo-mechanical forming of the alloy are primarily responsible for determining the alloy's characteristics. Processing history, including high temperature annealing as well as low temperature forming and deformation, also play a role in determining the crystallographic phase of the material. Following standard material and processing specifications, the transitional temperatures which define the alloy's mechanical characteristics are predictable and controllable. Standard transitional temperature designations are given as: $M_s$ for the start of the transition to the martensitic phase, $M_f$ for completion of the transition to martensite, $A_s$ for the start of the transition to the austenitic phase, and $A_f$ for the completed transition to austenite. Making the clip 10, 100, 200, 300, 400, 500, 600, 800 from non-superelastic materials such as stainless steel or spring steel is also contemplated by and therefore within the scope of the invention.

Superelasticity is also based on phase transition from austenite to martensite. Phase transition from austenite to martensite occurs when the alloy temperature is above $A_f$ and a physically restraining stress is applied to the alloy. As long as the restraint is in place, the portion of the alloy which is receiving the stress reverts to the martensitic phase, which remains as long as the stress is maintained. Unless the shape recovery limits are exceeded, when the stress is released the alloy returns to its original austenitic phase and shape as long as the temperature is maintained above $A_f$. Thus, when the austenitic, trained shape of the alloy is deformed and held by stress in a new shape, a certain amount of force is exerted by the alloy against the restraint as it resists the new, untrained shape. Similarly, following release of the restraint, should an object prevent the alloy from completely returning to its trained, austenitic shape (assuming the temperature is somewhere above $A_s$), the alloy will exert a certain amount of force against the object. This is another aspect of superelasticity and is caused by the temporary, stress induced formation of martensite which will revert back to austenite upon release of the restraint.

The thermal shape memory effect of these alloys has been known much longer than superelasticity. Thermal shape memory occurs as the result of a piece of shape memory alloy metal being deformed while in the lower temperature martensitic phase and then being reheated to a higher temperature which causes they alloy to reform in the austenitic phase. When the crystallographic nature of the alloy is completely austenitic, the alloy's shape returns to the shape prior to being deformed while in the martensitic phase. Shape memory training occurs when a shape memory/superelastic metallic alloy is annealed (heat treated) while restrained in a certain shape. The trained shape will then be maintained unless it is deformed while in the low temperature martensitic phase. Upon reheating the alloy to the austenitic phase, the original shape which was "learned" in the annealing process will be "remembered" and returned to. Thus, temperature change is one way of controlling the crystallographic phase of a shape memory/superelastic metallic alloy.

One practical advantage of a shape memory/superelastic alloy over non-superelastic materials is that it is able to be deformed to a far greater degree without taking a permanent set or kink. In the case of superelastic alloys (i.e., alloys processed to exhibit superelasticity at body temperature), assuming the alloy is above the $A_s$ temperature, removal of the restraint alone is sufficient to resume the original, trained shape. When the alloy is processed to have shape memory characteristics, the martensitic phase alloy need only be subjected to temperatures somewhere above $A_s$ and the alloy will eventually return to its original, trained shape. It is also possible to use a restraint in conjunction with alloys trained to exhibit thermal shape memory characteristics.

Thus, when the clip 10, 100, 200, 300, 400, 500, 600, 800 is processed to exhibit superelastic characteristics at human body temperature, it uses superelasticity in two different ways. First, superelasticity (stress-induced martensite) allows the clip 10, 100, 200, 300, 400, 500, 600, 800 to be deformed to a degree sufficient to enable it to be loaded into a surgical cannula 52, 352, without taking a permanent set or kink. While the clip 10, 100, 200, 300, 400, 500, 600, 800 is restrained within the lumen 56, 356 by the cannula walls 54, 354, assuming the clip 10, 100, 200, 300, 400, 500, 600, 800 is maintained at a temperature above $A_s$, the portions (unnumbered) of the clip 10, 100, 200, 300, 400, 500, 600, 800 contacting the lumen 56, 356 are exerting an amount of force against the cannula walls 54, 354 due to the formation of stress-induced martensite. The loaded cannula 52, 352 can then be introduced into the patient's body (not shown) through a small incision (not shown) following which the clip 10, 100, 200, 300, 400, 500, 600, 800 can be advanced from the distal end 58, 358 of the cannula 52, 352. Using non-invasive, minimally invasive, endoscopic or laparoscopic techniques, the physician is able to view the internal procedure. Using the push rod 60 and clip lock 62, the jaws 12, 14, 112, 114, 212, 214, 312, 314, 412, 414, 512, 514, 612, 614, 812, 814 of the clip 10, 100, 200, 300, 400, 500, 600, 800 are gradually advanced from the distal end 58, 358 of the cannula 52, 352. The clip 10, 100, 200, 300, 400, 500, 600, 800 can then be deployed around a suitable anatomical structure V to clamp or ligate the structure V. As explained below, the force exerted by the deployed clip 10, 100, 200, 300, 400, 500, 600, 800 against the clamped anatomical structure V is also a function of superelasticity (stress-induced martensite), due to the presence of the anatomical structure V between the jaws.

A further superelastic phenomenon affects the performance of the clamping ability of the clip. Superelastic nitinol is unusual in that an increased amount of stress applied to a certain point does not obey Hooke's law, which predicts an increased proportional corresponding amount strain to be exerted by the alloy. Instead, hysteresis is exhibited as a result of the formation of stress-induced martensite, where a stress plateau is formed as a result of increased strain. Put another way, a larger structure requires an increased amount of deflection of the jaws 12, 14, 112, 114, 212, 214, 312, 314, 412, 414, 512, 514, 612, 614, 812, 814 to be able to surround the structure (not shown). By using superelastic nitinol, the amount of force exerted by the clip 10, 100, 200, 300, 400, 500, 600, 800 is approximately the same as if a relatively small structure (not shown) is being clamped. The practical effect of this phenomenon is that the amount of clamping force is programmable and predictable as a result of the thermo-mechanical processing of the alloy. Thus, a clip 10, 100, 200, 300, 400, 500, 600, 800 can be designed which is programmed to exert only the amount of force necessary to complete the clamping procedure, but which is known to be below an amount that would damage the clamped tissue. Further control over the amount of force exerted by the clip 10, 100, 200, 300, 400, 500, 600, 800 can be adjusted by altering mechanical parameters such as wire diameter, and additional shape parameters such as size and angle of the flexing portions 20, 22, 120, 122, 320, 322, 420, 422, 520, 620, 820, 822. Having a "coiled spring" section (not shown) around the proximal end 26, 126, 226, 426, 526, 626 and 826 is an additional design parameter that could be used to control the amount of force exhibited by the clip 10, 100, 200, 300, 400, 500, 600, 800 and is therefore contemplated by and within the scope of the invention.

When the clip 10, 100, 200, 300, 400, 500, 600, 800 is formed to exhibit shape memory characteristics at body temperature, the $A_s$ must be programmed into the alloy to be somewhere below human body temperature. The clip 10, 100, 200, 300, 400, 500, 600, 800 is loaded into a surgical cannula 52, 352 at a temperature somewhere above $A_s$ as described above. Alternatively, the clip 10, 100, 200, 300, 400, 500, 600, 800 can be cooled to a temperature below $M_f$ to place the clip 10, 100, 200, 300, 400, 500, 600, 800 in the martensitic phase prior to loading. When the loaded cannula 52, 352 is being inserted into the body (not shown), means must be used to maintain the temperature of the clip below $A_s$. Typically, a cold saline drip (not shown) is maintained through the lumen 56, 356 during the insertion procedure. Following arrival of the loaded cannula 52, 352 at the treatment site within the patient's body, the clip 10, 100, 200, 300, 400, 500, 600, 800 is advanced from the distal end 58, 358 of the cannula whereupon it is exposed to body temperature, which is above the $A_s$ of the alloy. Exposure to body temperature raises the temperature of the alloy to a point where the unstressed portions of the clip 10, 100, 200, 300, 400, 500, 600, 800 are in the austenitic phase, returning the clip 10, 100, 200, 300, 400, 500, 600, 800 toward its original, trained shape.

Making the clip 10, 100, 200, 300, 400, 500, 600, 800 involves acquiring a sufficient length of nitinol wire (not shown) and securely installing it in a jig (not shown) having stops (not shown) matching the contours of the desired finished, trained shape. Wire of varying diameters and shapes (e.g., rectangular (not shown), half round (not shown), full round 912, ribbon 910 or D-shaped 914) is heated at various temperatures and lengths of time due to differences in size and metallurgy and desired mechanical performance. The wire (not shown) is then cooled by various methods depending on the desired finished characteristics. Finally, the distal ends 24a, 24b, 124a, 124b, 224a, 224b, 324a, 324b, 424a, 424b, 524a, 524b, 624a, 624b, 824a, 824b of the clip 10, 100, 200, 300, 400, 500, 600, 800 are preferably rounded or blunt, however, sharp tips may also be required in some cases requiring puncturing of tissue as part of a procedure. It should mentioned that wire having a relatively high porosity (i.e., not polished or oxided) is preferable due to its improved ultrasonography characteristics. It is also contemplated by and therefore within the scope of the invention to roughen the surface of the clip 10, 100, 200, 300, 400, 500, 600, 800 to improve the ultrasonography characteristics. Where grippability is critical, it possible to create teeth (not shown) on the surfaces of the clamping portions 16, 18, 116, 118, 216, 218, 316, 318, 416, 418, 516, 518, 616, 618, 816 and 818.

Use

Figure 5:
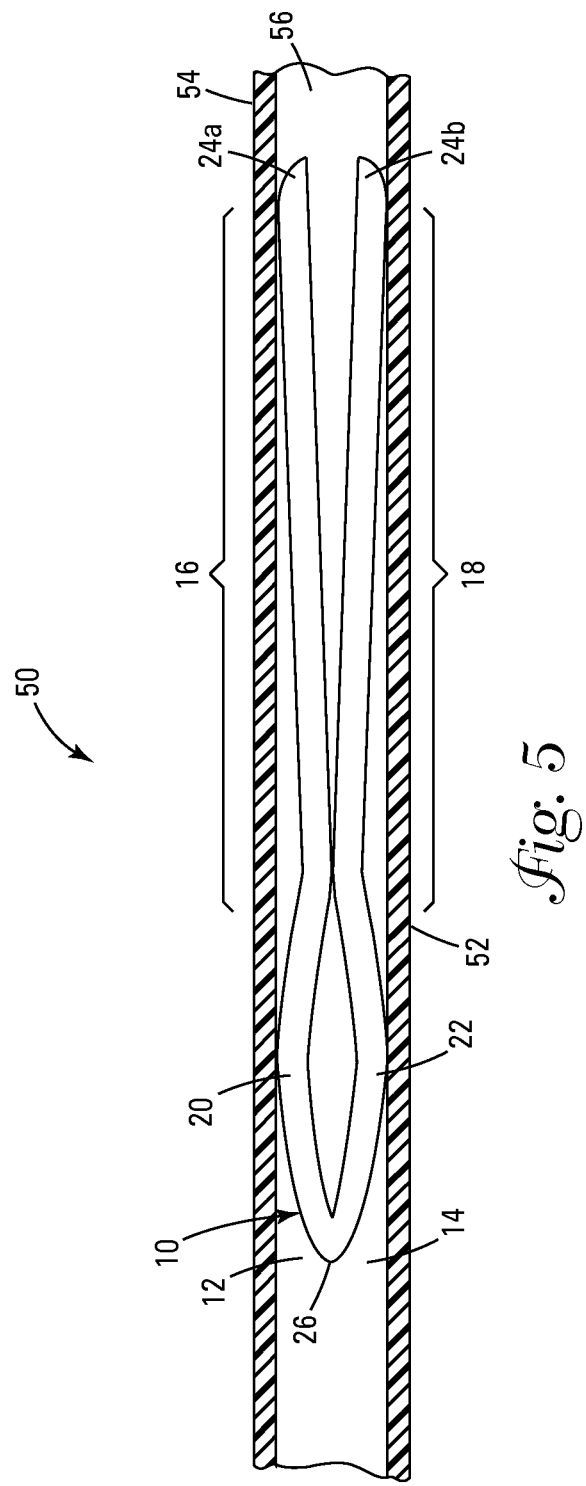
FIG. 5 shows a side cutaway view of the ligation clip loaded into a cannula.

Using the clip 10, 100, 200, 300, 400, 500, 600, 800 involves first loading the clip 10, 100, 200, 300, 400, 500, 600, 800 into a surgical cannula 52, 352. The term surgical cannula 52, 352 as used here is generic and refers to any tubular structure defining a lumen used to gain access to remote sites in a patient's body, such as a needle, catheter, sheath or other delivery system. Depending on the type of cannula 52, 352 used, the clip 10, 100, 200, 300, 400, 500, 600, 800 can be loaded into either the proximal end (not shown) or the distal end 58, 358 of the cannula 52, 352. The finally loaded clip system 50 is best shown in FIG. 5. Regardless of which end of the cannula 52, 352 is used for loading, the clip 10, 100, 200, 300, 400, 500, 600, 800 is inserted so the distal ends 24a, 24b, 324a, 324b, 424a, 424b, 524a, 524b, 624a, 624b, 824a, 824b exit first from the distal end 58, 358 of the cannula 52, 352 following advancement.

Following loading of the cannula 52, 352, the clip system 50 is navigated to the remote treatment site (not shown) in the patient's body, using well known techniques. Using noninvasive, minimally invasive, endoscopic or laparoscopic techniques the physician is able to visualize the treatment site. Upon determining the anatomical structure to be clamped, the physician uses the push rod 60 and clip lock 62 which are attached to a mechanical stop system (not shown) to precisely advance the distal ends 24a, 24b, 324a, 324b, 424a, 424b, 524a, 524b, 624a, 624b, 824a, 824b of the clip 10, 100, 200, 300, 400, 500, 600, 800 from the distal end 58, 358 of the cannula 52, 352. Advancing the clip 10, 100, 200, 300, 400, 500, 600, 800 a very small distance while visualizing the procedure, the clamping portions 16, 18, 116, 118, 216, 218, 316, 318, 416, 418, 516, 518, 616, 618, 816, 818 of the jaws 12, 14, 112, 114, 212, 214, 312, 314, 412, 414, 512, 514, 612, 614, 812, 814 upon being released from the confines of the cannula 52, 352 extend away from the cannula 52, 352 as best shown in FIG. 6. The clamping portions 16, 18, 116, 118, 216, 218, 316, 318, 416, 418, 516, 518, 616, 618, 816, 818 of the jaws 12, 14, 112, 114, 212, 214, 312, 314, 412, 414, 512, 514, 612, 614, 812, 814 extend in this direction due to the continued compression of the flexing portion of the jaws 20, 22, 120, 122, 220, 222, 320, 322, 420, 422, 520, 620, 820, 822 by the lumen 56, 356 of the cannula 52, 352. The open configuration of the clamping portions 16, 18, 116, 118, 216, 218, 316, 318, 416, 418, 516, 518, 616, 618, 816, 818 allows the physician to position the clamping portions 16, 18, 116, 118, 216, 218, 316, 318, 416, 418, 516, 518, 616, 618, 816, 818 of the clip 10, 100, 200, 300, 400, 500, 600, 800 around the anatomical structure V to be clamped. When the anatomical structure V to be clamped is surrounded, the physician further advances the clip 10, 100, 200, 300, 400, 500, 600, 800 from the cannula 52, 352, eventually resulting in the flexing portions of the jaws 20, 22, 120, 122, 220, 222, 320, 322, 420, 422, 520, 620, 720, 820, 822 being released from the lumen 56, 356 of the cannula 52, 352 and thereby being decompressed. As best shown in FIG. 7, decompression results in the clamping portions 16, 18, 116, 118, 216, 218, 316, 318, 416, 418, 516, 518, 616, 618, 816, 818 attempting to resume their original, trained, austenitic phase configuration. The clamping portions 16, 18, 116, 118, 216, 218, 316, 318, 416, 418, 516, 518, 616, 618, 816, 818, however, are prevented from completely closing due to the presence of the clamped anatomical structure V being clamped by the clamping portions 16, 18, 116, 118, 216, 218, 316, 318, 416, 418, 516, 518, 616, 618, 816, 818. This is results in the formation of stress-induced martensite, which supplies the force exerted by the clip 10, 100, 200, 300, 400, 500, 600, 800 against the anatomical structure. Finally, the clip lock 62 is released as shown in FIG. 8.

Repositioning the clip 10, 100, 200, 300, 400, 500, 600, 800, prior to release from the clip lock 62, is a relatively easy procedure. Using the push rod 60, the physician draws the flexing portions of the jaws 20, 22, 120, 122, 220, 222, 320, 322, 420, 422, 520, 620, 820, 822 back into the lumen 56, 356 until the clamping portions 16, 18, 116, 118, 216, 218, 316, 318, 416, 418, 516, 518, 616, 618, 816, 818 are again spread apart as best shown in FIG. 6. This allows the physician to reposition the clip 10, 100, 200, 300, 400, 500, 600, 800 over another anatomical site, and repeat the procedure described above.

What is claimed is:

1. A method of using a clip system for applying a clip device to mammalian tissue, comprising:
   providing a needle including a bore that extends longitudinally to a distal opening of the needle, the distal opening being deliverable to a targeted internal tissue; and
   inserting a clip device through the needle bore, wherein the clip device superelastically deforms to a lateral dimension smaller than an inner dimension of the needle bore so that the entire clip device advances into the needle bore for delivery out of the distal opening of the needle, the clip device including:
   a first clamping arm and a second clamping arm opposing the first clamping arm and being biased toward the first clamping arm, the first and second clamping arms including proximal portions that abut against one another and distal ends that are movable away from one another, and a flexing head coupled to proximal ends of the first and second clamping arms, the flexing head being adjustable between a first shape in which the first and second clamping arms extend generally parallel to one another and a stressed shape in which at least the distal ends of the first and second clamping arms are spaced apart while the proximal portions of the first and second clamping arms abut against one another, wherein, during the step of inserting the clip device when the entire clip device is disposed in the needle bore, the needle engages the flexing head to releasably retain the flexing head in the stressed shape; and advancing the clip device distally out of the distal opening of the needle so that the flexing head adjusts toward the first shape so that the first and second clamping arms shift toward one another to provide a clamping force.

2. The method of claim 1, further comprising engaging a push rod with the clip device when the clip device is inserted into the bore of the needle.

3. The method of claim 2, wherein the push rod comprises a clip lock to releasably engage the flexing head of the clip device when the clip device is inserted into the bore of the needle.

4. The method of claim 1, wherein the flexing head comprises a first flexing section coupled to the proximal portion of the first clamping arm and a second flexing section coupled to the proximal portion of the second clamping arm, the first flexing section of the clip device mirrors the shape of the second flexing section relative to a longitudinal axis.

5. The method of claim 4, wherein the first clamping arm is aligned with the second clamping arm along the longitudinal axis so that the first clamping arm contacts the second clamping arm without crossing over the longitudinal axis.

6. The method of claim 1, wherein the clip device comprises a single wire that defines the first jaw and the second jaw, the wire having a cross-sectional shape in a lateral plane of the clip device.

7. The method of claim 6, wherein the cross-sectional shape in the lateral plane is D-shaped.

8. The method of claim 1, wherein the clip device is configured to engage an anatomical structure when the first and second clamping arms shift toward one another.

9. The method of claim 1, wherein the proximal portions of the first clamping arm and the second clamping arm abut against one another when the flexing head is in the stressed shape.

10. The method of claim 9, wherein the distal ends of the first clamping arm and the second clamping arm comprise blunt tips.

11. The method of claim 1, wherein the clip device comprises a material that exhibits superelasticity characteristics at a temperature of about 37 degrees C., the flexing head exhibiting superelasticity characteristics when the flexing head returns toward the first shape after being deformed to the stressed shape while the entire clip device is disposed in the needle bore.

12. The clip system of claim 1 further comprising a push rod movably disposed in the needle bore to deliver the clip device distally from the needle bore and out of the distal opening.

13. The method of claim 1, wherein the first clamping arm comprises wave-shaped grips that are matable with complementary wave-shaped grips of the second clamping arm.

14. The method of claim 13, wherein the wave-shaped grips facilitate engagement with the targeted internal tissue between the first and second clamping arms.

15. The method of claim 1, wherein the first clamping arm comprises an indentation that at least partially defines a gap between the first clamping arm and the second clamping arm.

16. The method of claim 15, wherein the gap that is at least partially defined by the indentation provides a seat structure that retains the targeted internal tissue engaged between the first and second clamping arms.

17. The method of claim 1, wherein in the clip device comprises a superelastic alloy material that is mechanically processed to provide a predetermined clamping force between the first and second clamping arms.

18. The method of claim 17, wherein the predetermined clamping force is selected to provide a force that is sufficient to clamp the targeted internal tissue between the first and second clamping arms and that is below a threshold force to damage the targeted internal tissue.

* * * * *